United States Patent [19]
Pero

[11] Patent Number: 6,039,949
[45] Date of Patent: Mar. 21, 2000

[54] METHOD OF PREPARATION AND COMPOSITION OF A WATER SOLUBLE EXTRACT OF THE PLANT SPECIES UNCARIA

[75] Inventor: Ronald W. Pero, Lund, Sweden

[73] Assignee: CampaMed, Inc., New York, N.Y.

[21] Appl. No.: 08/807,373

[22] Filed: Feb. 27, 1997

[51] Int. Cl.[7] .................................................. A61K 35/78
[52] U.S. Cl. ...................... 424/195.1; 514/885; 514/886; 514/908
[58] Field of Search .............................. 424/195.1; 435/4, 435/7.21, 7.23, 7.24, 390; 514/885, 886, 908

[56] References Cited

U.S. PATENT DOCUMENTS

| | | | |
|---|---|---|---|
| 4,844,901 | 7/1989 | Keplinger et al. | 424/195.1 |
| 4,940,725 | 7/1990 | Keplinger et al. | 514/411 |
| 5,302,611 | 4/1994 | Keplinger et al. | 514/411 |
| 5,411,733 | 5/1995 | Hozumi et al. | 424/195.1 |

FOREIGN PATENT DOCUMENTS

| | | |
|---|---|---|
| 56032418 | 4/1981 | Japan. |
| Wo 82/01130 | 4/1982 | WIPO. |

OTHER PUBLICATIONS

Kuramochi et al., Life Sciences, 54:2061–2069, 1994.
Rizzi et al., Journal of Ethnopharmacology, 38:63–77, 1993.
Kiuchi et al., Chem. Pharm. Bull., 31:3391–3396, 1983.
New Polyhydroxylated Triterpenes From Uncaria Tomentosa, R. Aquino, F. De Simone, F.F. Vincieri, C. Pizza, Journal of Natural Products, vol. 53, No. 3, pp. 559–564, May–Jun. 1990.
Plant Metabolites Structure And In Vitro Antiviral Activity Of Quinovic Acid Glycosides From Uncaria Tomentosa And Guettarda Playtypoda, R. Aquino, F. De Simone, C Pizza, Journal of Natural Products, vol. 52, No. 4, pp. 679–685, Jul.–Aug. 1989.
Plant Metabolites New Compounds And Antiflammatory Activity of Uncaria Tomentosa, Rita Aquino, Vicenzo De Feo, Francesco De Simone, Cosimo Pizza, and Giuseppe Cirino, Journal of Natural Products, vol. 54, No. 2, pp. 453–459, Mar.–Apr. 1991.
Francesco De Simone, Cosimo Pizza, and Giuseppe Cirino, Journal of Natural Products, vol. 54, No. 2, pp. 453–459, Mar.–Apr. 1991.
Plant–Derived Natural Products in Drug Discovery and Development, Manuel F. Balandrin, A. Douglas Kinghorn and Norman R. Farnsworth, 1993 American Chemical Society (Chapter 1).
Phytomedicines in Western Europe—Potential Impact on Herbal Medicine in the United States, Varro E. Tyler Dept. of Medicinal Chemistry and Pharmacognosy, School of Pharmacy and Pharmacal Sciences, Purdue University, West Lafayette, IN 47907–1333, 1993 American Chemical Society (Chapter 3).
Role of Plants in the National Cancer Institute Drug Discovery and Development Program, Gordon M. Cragg, Michael R. Boyde, John H. Cardellina II, and Matthew Suffnmess, Published 1993 American Chemical Society (Chapter 7).
Una de Gato (Cat's Claw) Rainforest herb gets scientific and industry attention, by Mark Blumenthal, Whole Foods Magazine, Oct. 1995, pp. 62,64,66,68 & 78.
Apoptosis and a re–investigation of the biologic basis for cancer therapy, Anthony V. D'Amico, W. Gillies McKenna Radiotherapy and Oncology 33 (1994) 3–10.
Apoptosis in the Pathogenesis and Treatment of Disease, Craig B. Thompson, Science, vol. 267, Mar. 10, 1995.

*Primary Examiner*—Jon P. Weber
*Assistant Examiner*—Janet M. Kerr
*Attorney, Agent, or Firm*—Cobrin & Gittes

[57] ABSTRACT

The present invention is directed to a method of preparation and the composition of a water soluble extract of the plant species Uncaria. The present invention is also directed to the pharmaceutical use of the composition for the enhancement of the immune, anti-inflammatory, anti-tumor and DNA repair processes of warm blooded animals. The present preparation of the water soluble extract of the plant species Uncaria results in the depletion of many of the ingredients which lead to various toxic side effects associated with other extracts or compositions derived from Uncaria. Also, the present preparation leads to the depletion of many of the active ingredients commonly associated with other extracts and compositions of the plant species Uncaria. Therefore, the present invention teaches that the hot water extraction of the crude plant parts of Uncaria and the subsequent dialysis of the solubilized products yields a low molecular weight composition which maintains a high degree of the anti-tumor, inflammatory and immune stimulatory activities associated with the crude plant parts.

18 Claims, 9 Drawing Sheets

\* P <= 0.05 BY ONE-TAILED T-TEST; \*\*P < 0.05 BY TWO-TAILED T-TEST, COMPATED WITH CONTROL GROUP.

METHOD OF PREPARATION AND COMPOSITION OF A WATER SOLUBLE EXTRACT OF THE PLANT SPECIES UNCARIA

BACKGROUND AND FIELD OF THE INVENTION

1. Field of the Invention

The present invention deals with defining a phytomedicinal water extract preparation of the plant species Uncaria. In this preparation, many of the ingredients leading to non-specific toxic side effects including palability generated from the presence of such ubiquitous plant toxic compounds as polysacharrides and tannins are depleted (Cragg et al, Amer. Chem. Soc. Symposium Series 534 :81–96, 1993). In addition, the most common biologically active plant products (e.g. steroids and alkaloids) are also depleted. This is accomplished by hot water extraction of the crude plant parts of Uncaria and subsequent dialysis of the solubilized products where a high degree of anti-tumor and immune stimulatory activities are maintained in the final dialyzed (low molecular weight) fraction.

2. Discussion of Related Art

Drugs derived from higher plants represent about 25% of all prescription drugs dispensed by pharmacies in the United States. For example, over 35,000 plant species have been screened between 1960 and 1986 for cytotoxic and antitumor properties which adds additional support to the concept that plant extracts are a potential rich source of medicines (Balandrin et al, Amer.Chem. Soc. Symposium Series 534:3–11, 1993). Most of the clinically useful plant products discovered so far have either been phytomedicines defined as ingested crude plant parts or as plant extract/tincture preparations (e.g. Gingko, Echinacea, Chamomile, St. John's Wort, Saw Palmetto, Hawthorn, Lemon Balm), or as isolated chemical entities of two major chemical categories—namely the steroids and alkaloids (Balandrin et al, Amer. Chem. Soc. Symposium Series 534:3–11, 1993; V. E. Tyler, Amer.Chem. Soc. Symposium Series 534:24–38, 1993).

There is prior art establishing that extracts of the plant species Uncaria contain alkaloids, sterols, and triterpenoids which in turn are known to possess antiviral, anti-inflammatory, anti-mutagenic and anti-tumor (cytotoxic) activities (K.Keplinger, PCT Int. Appl. WO 8210, 130, 1985; Wagner et al, Planta Med. 419–23, Oct. 5 1985; Senatore et al Boll.Ital. Biol. Sper. 65(5):517–20, 1989; Aquino et al, J. Nat. Prod. 52(4):679–85, 1989; Aquino et al, J. Nat. Prod. 53(3):559–64, 1990; Aquino et al, J. Nat. Prod. 54(2):453–9, 1991; Rizzi et al, J. Ethanopharmacol. 38(1) :63–77, 1993). In fact, the available scientific literature teaches that the medicinal properties of the plant species Uncaria are due to the presence of these biologically active ingredients in phytomedicinal preparations of this plant. However, these components of Uncaria are usually extracted from the plant parts with organic solvents because of their poor solubility in water. It follows then that this prior art does not teach one skilled in the art that a low molecular weight, water soluble fraction of Uncaria would have any antitumor or immune stimulatory properties. Therefore, the discovery disclosed in this invention, that there is a high degree of biological activity in the hot water, low molecular weight fraction of Uncaria, is not obvious but novel and proprietary.

Phytomedicinal preparations of Uncaria (also known as Una de Gato and Cat's Claw) have been sold in the United States and other countries for years as a herbal medicine. The basic formulation of these products has been encapsulated pulverized plant parts administered orally as 1–3 grams of crude bark per day. This method of preparation and dosing is a serious deviation from the historical medicinal use of Uncaria species described by the Indians indigenous to the Amazon basin of South America. Native Indians prepare treatments of Uncaria by drinking hot water extracts as a tea (1 cup or about 100 ml containing about 0.1–0.4 grams of crude plant parts per day). There is a 10–20 fold increase in the daily doses offered commercially compared to the practice of historical medicinal use. However, commercial Uncaria preparations rely on an efficient extraction and absorption of the active ingredients under the strong acidic conditions existing in the stomach. In contrast, the historical Uncaria medicinal preparations rely on hot water extracting the active components from the particulate fraction before they are ingested. There is no a priori scientific reason to believe that commercial preparations of Uncaria duplicate the historical practice of administering efficacious water-extracted doses to humans. For example, it is not obvious or taught by this prior art that acidic digestion of Uncaria crude plant parts in the stomach would even approximate the efficiency of hot water extraction. In addition, the hot water insoluble materials left behind when preparing tea extracts which are present in commercial crude plant part preparations, might cause stomach irritation, toxicity or limit the absorption of Uncaria's active ingredients. It is significant that a recent review of the literature has revealed that there has never been a single peer-reviewed scientific article demonstrating any efficacious effects from human oral consumption of crude plant parts of Uncaria.

SUMMARY OF THE INVENTION

In one aspect, the present invention teaches that if the plant species of Uncaria are hot water extracted, which has been the practice from historical medicinal use, and then dialyzed to deplete ubiquitous non-specific toxic components and the levels of previously identified lipophilic components such as sterols and alkaloids possessing anti-tumor and anti-inflammatory properties, there still remains in the dialyzable fraction a novel phytomedicinal preparation of Uncaria having potent anti-tumor and immune stimulatory properties without any measurable toxic side effects. Any potential medicinal properties possessed by this subfractioned formulation of Uncaria would likely have been depleted of many of the known active ingredients of Uncaria, namely the sterols and alkaloids, because it is a low molecular weight water soluble preparation.

In another aspect, this invention discloses the method by which warm blooded animals could be treated successfully by oral administration of Uncaria water extracts. Here, it is disclosed that the water soluble portion of crude Uncaria bark at 3736 $\mu$g of crude bark per ml (calculated from 198 $\mu$g per milliliter dried water extract of C-Med-100, FIG. 1, Example 2 and the yield of C-Med-100 extract from crude bark=5.3%, Example 1) is necessary in order to inhibit 50% of tumor cell growth in vitro following a single dose. This would translate into a 70 kg person having to take 262 one gram capsules containing crude pulverized bark per day. It follows then that this invention permits the methodological advantage of delivering a safe and more efficacious in vivo treatment of Uncaria at doses 100 times higher than have ever been previously achieved with either commercial or historical preparations. Moreover, being water soluble, the new dialyzable fraction of Uncaria plant parts could be easily dried and combined with non-toxic inert carrier or diluent for convenient oral administration. Examples of such non-toxic, inert carriers include, but are not limited to, wheat starch and sodium carboxymethyl cellulose.

Figure 1B:
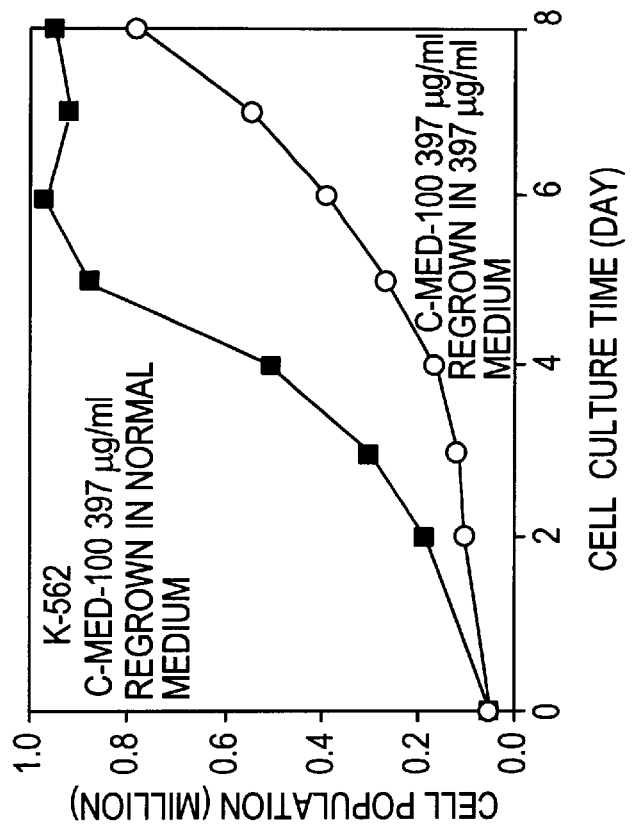
FIG. 1. The effect of C-MED-100 extract (Example 1) on cell proliferation. The left panel shows the growth curves while the right panel shows the regrowth curves. At the last day of the experiment, cells in the groups having C-MED-100 extract at 397 μg/ml were spun down, counted and resuspended in normal medium or medium with C-MED-100 extract at 397 μg/ml. Cell survival was assessed by trypan blue exclusion.
Figure 1A:
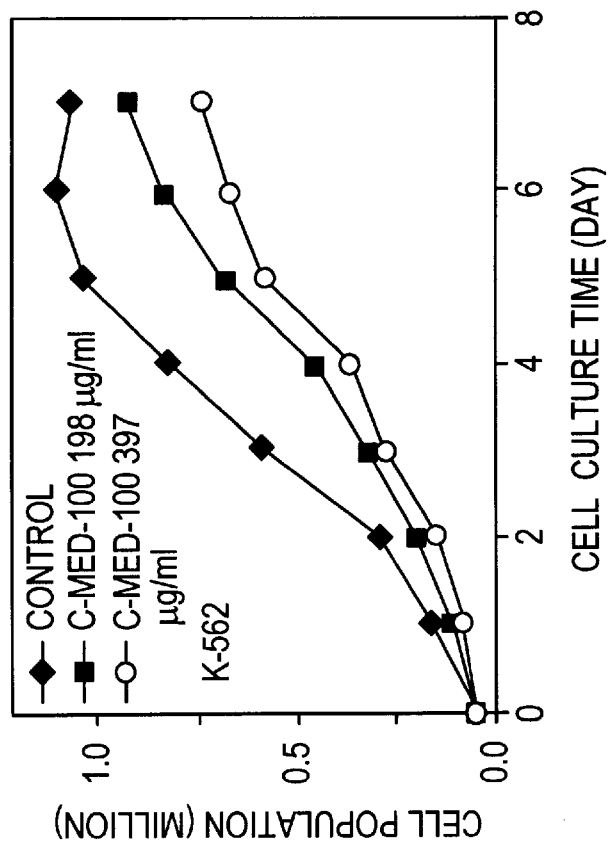
Figure 1D:
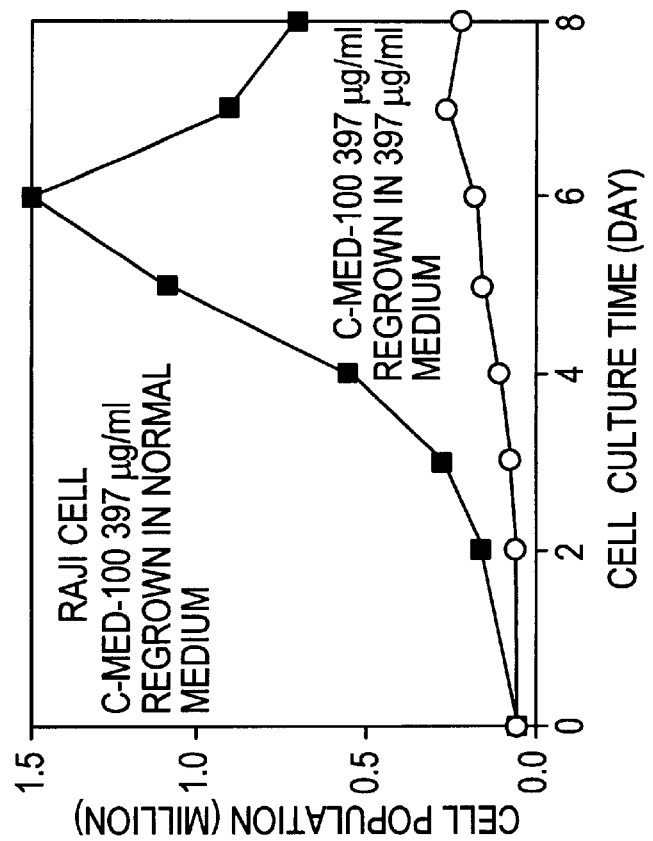
Figure 1C:
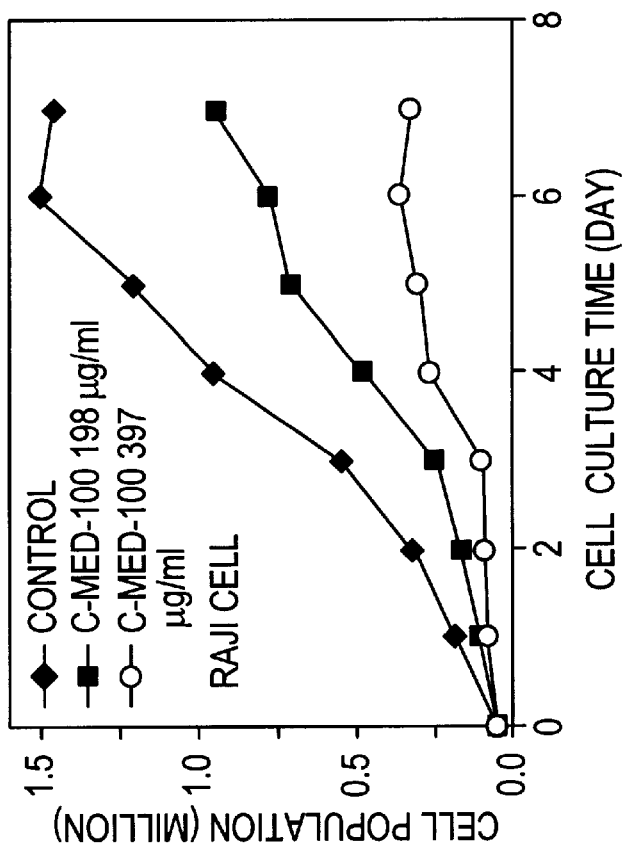
Figure 1F:
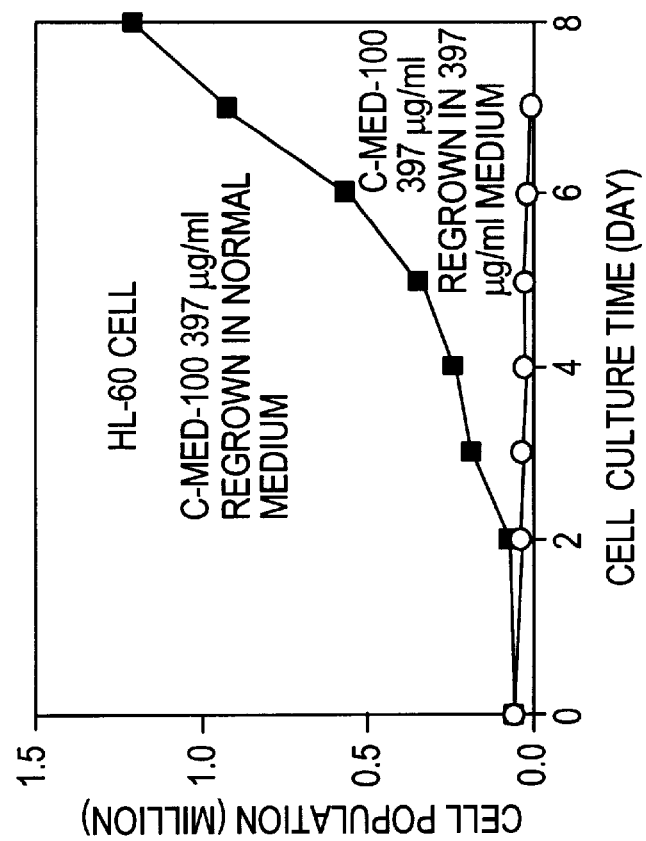
Figure 1E:
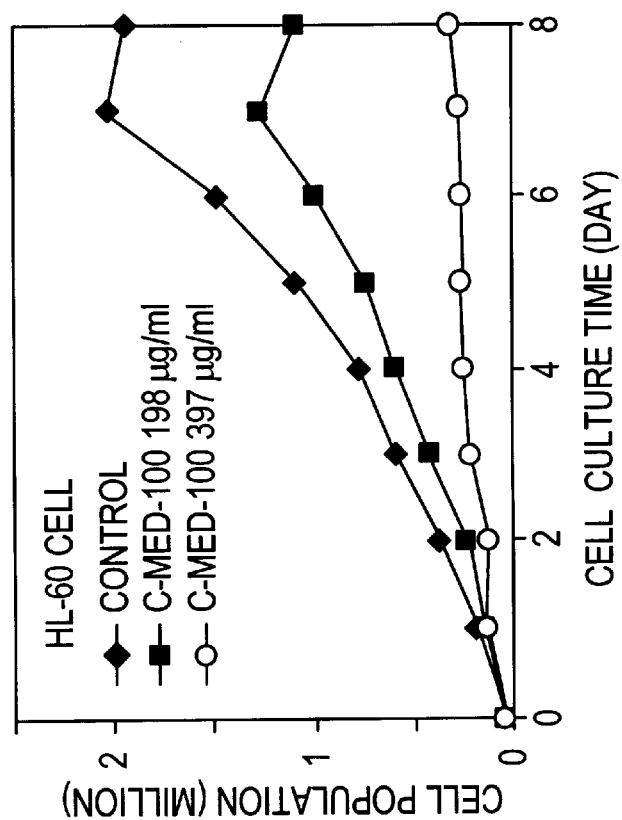
Figure 2:
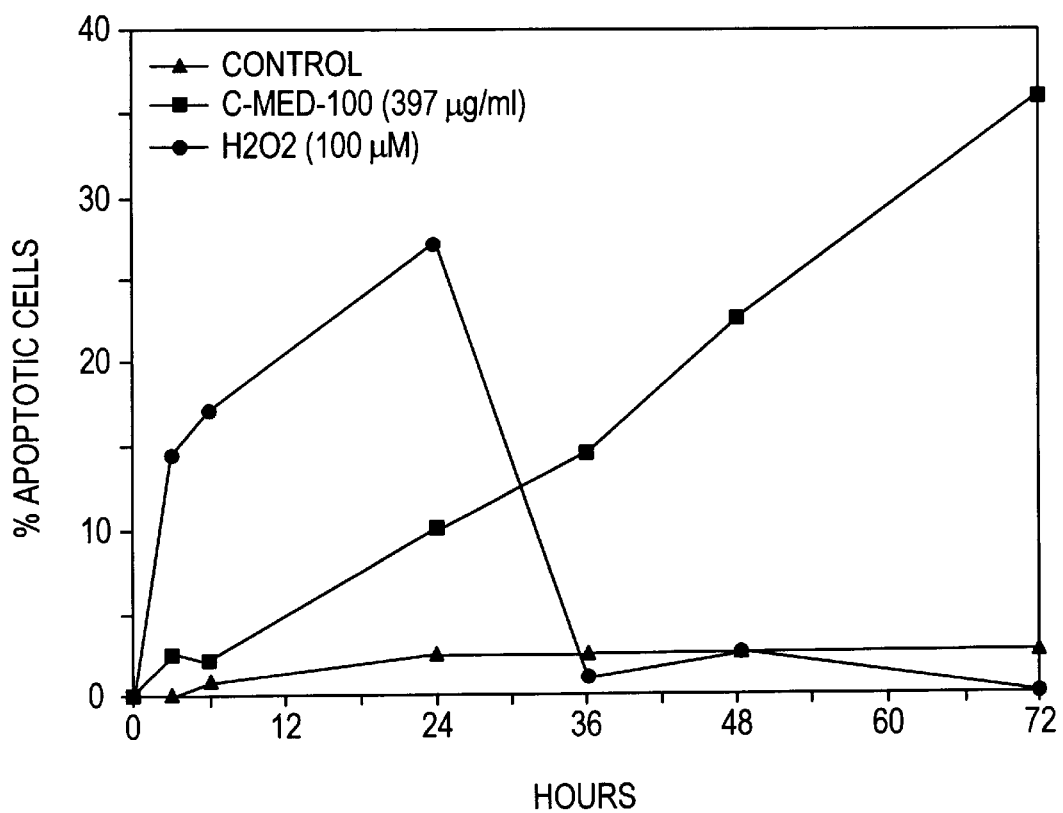
FIG. 2. Time course of apoptosis in HL-60 cells induced by C-MED-100 extract (Example 1) as compared to negative (no treatment) or positive (100 μM $H_2O_2$ exposure) controls.

The data displayed in FIG. 2 teaches that C-Med-100 extract induces a time dependent increase in apoptotic cells over the entire evaluation period of 72 hours. Hydrogen peroxide, which was used as a positive control, caused massive cell death by apoptosis within 24 hours, after which time no more apoptosis occurred. This difference in response over time between C-Med-100 extract, and the classic apoptotic agents represented here by hydrogen peroxide, supports the hypothesis that the mode of action of induction of apoptosis by C-Med-100 extract is unique. In this regard, it offers the advantage of developing a phytomedicine having a selective mode of inducing cytotoxicity by apoptosis that, in turn, influences the progression of disorders such as inflammation, cancer and immunosuppression. In addition, these studies were performed on human leukemic cells (HL-60) which also directly demonstrates the ability of C-Med-100 extract to kill tumor cells.

Figure 3:
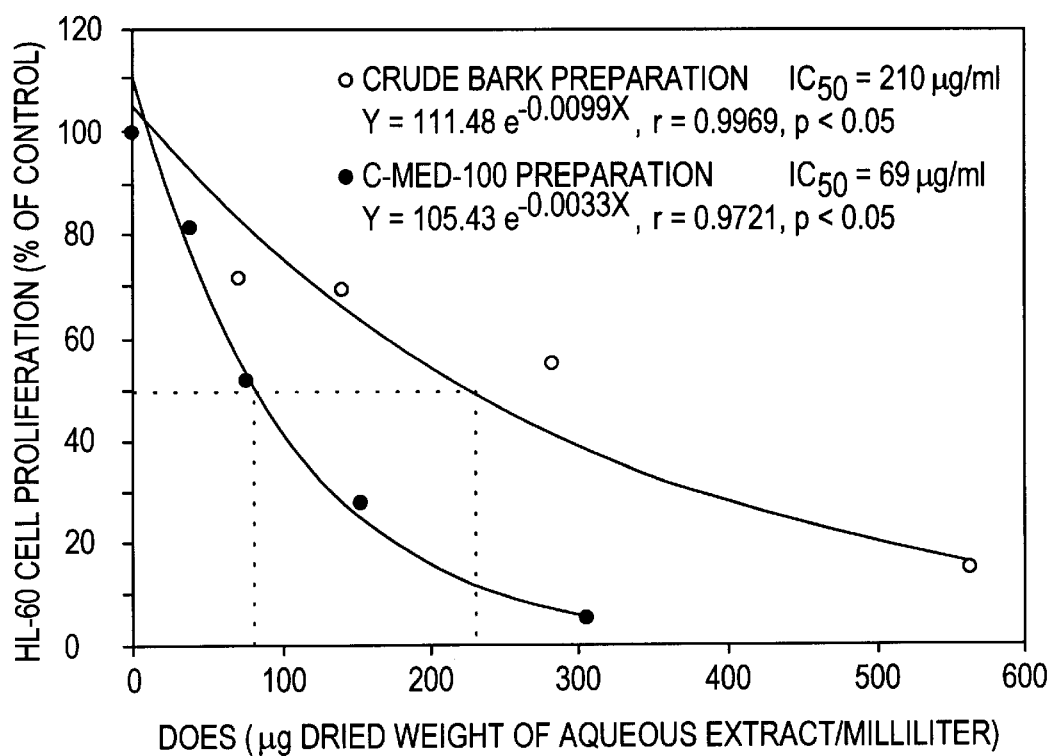

FIG. 3. Dose response of acidic preparations of crude bark and C-MED-100 extract (Example 1) of Uncaria to inhibit the growth of leukemic HL-60 cells. Cell proliferation was assessed by the [$^3$H]thymidine incorporation into DNA after 3 days of culture and 1 hour labelling. The data points represent the average of 3 samples and expressed as percentage of controls.

The data reported in FIG. 3 show that the $IC_{50}$ values (i.e. the dose inducing 50% inhibition of cell proliferation) for C-Med-100 extract modified to equal the oral ingestion of an equivalent crude bark preparation of Uncaria was about three times more biologically active at inhibiting tumor cell growth. This result teaches the superior method of using C-Med-100 extract in preference to the current phytomedicinal preparations for oral ingestion of Uncaria because smaller initial doses of the C-Med-100 extract can be practically employed more effectively to achieve in a single dose of even greater efficacious health benefits such a preventive antitumor treatment.

Figure 4:
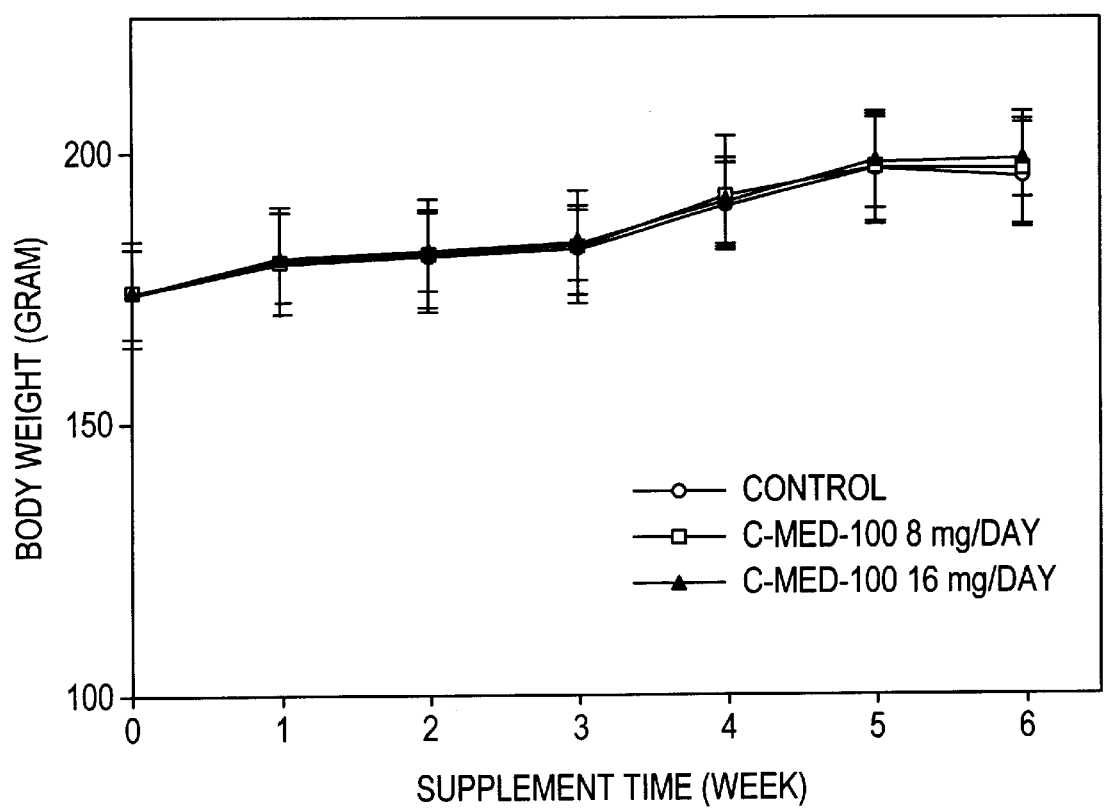

FIG. 4. Body weight change after C-MED-100 extract (Example 1) was supplemented daily to W/Fu rats for 6 weeks.

Figure 5A:
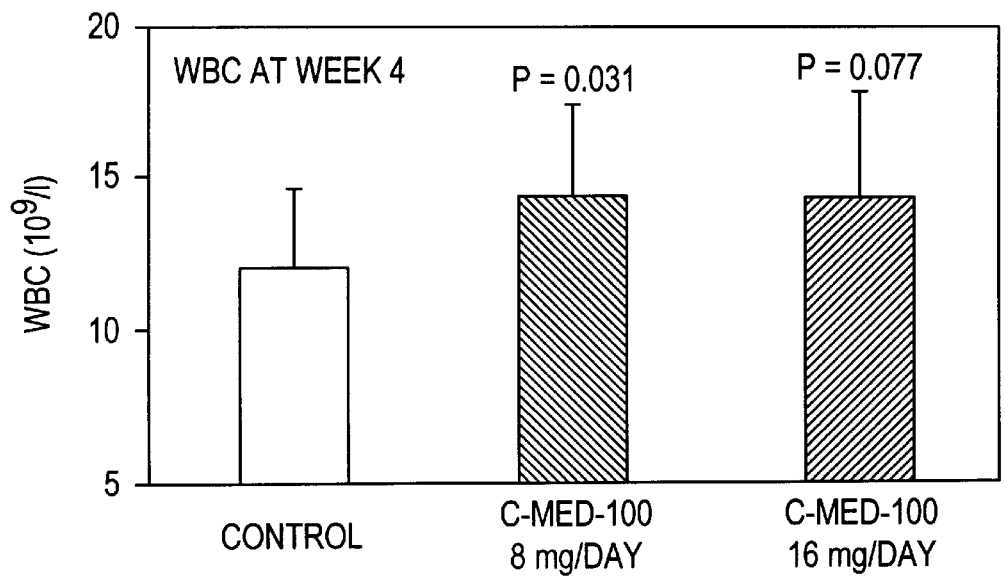
Figure 5B:
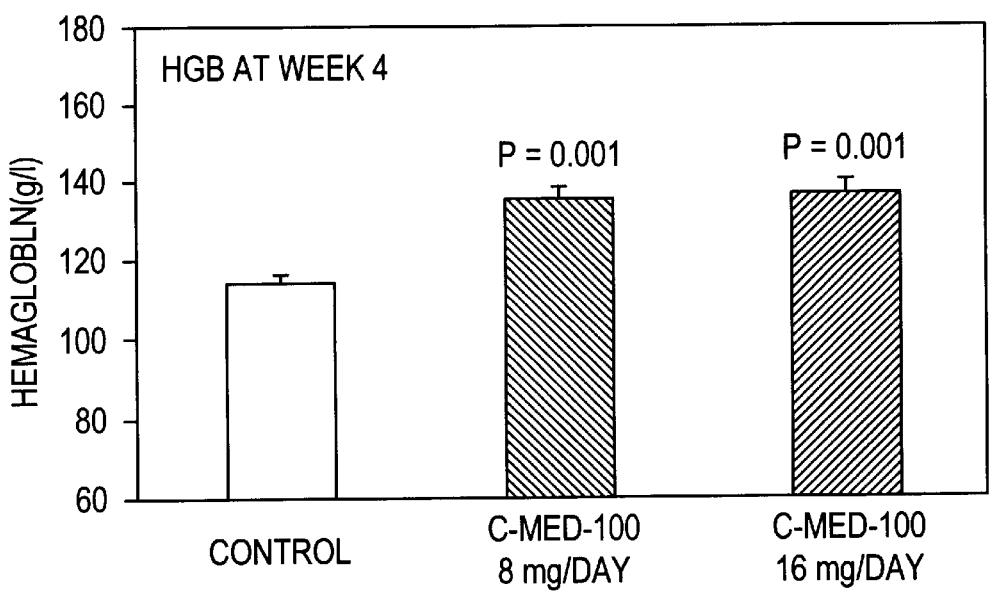

FIG. 5. Haemoglobin (HGB) and white blood cell (WBC) counts of blood after 4 weeks of daily supplementation of C-MED-100 extract (Example 1) to W/Fu rats. Blood was sampled from rat orbital vessels in heparinized tube and measured by an automated haematological analyzer. Data shown are average in column and standard deviation (SD) in error bar (n=8–10). P values shown are by one-tailed t-test.

Figure 6:
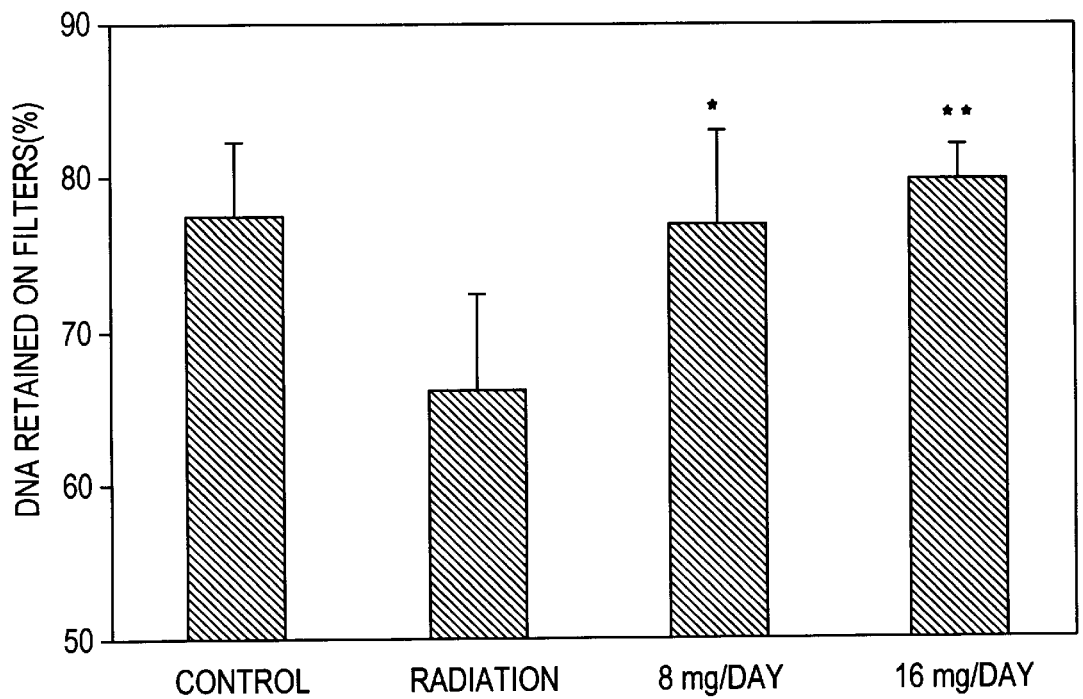

FIG. 6. DNA repair enhancement by C-MED-100 extract (Example 1) supplementation in a rat model. DNA damage and repair were measured by alkaline elution of spleen single cell suspensions from female W/Fu rats. C-MED-100 supplemented rats (8 and 16 mg/day for 8 weeks) were irradiated with or without 12 Grays and allowed to repair in vivo for 3 hours. Data shows the averages in column and SD by error bar (n>=5 in each group).

Figure 7:
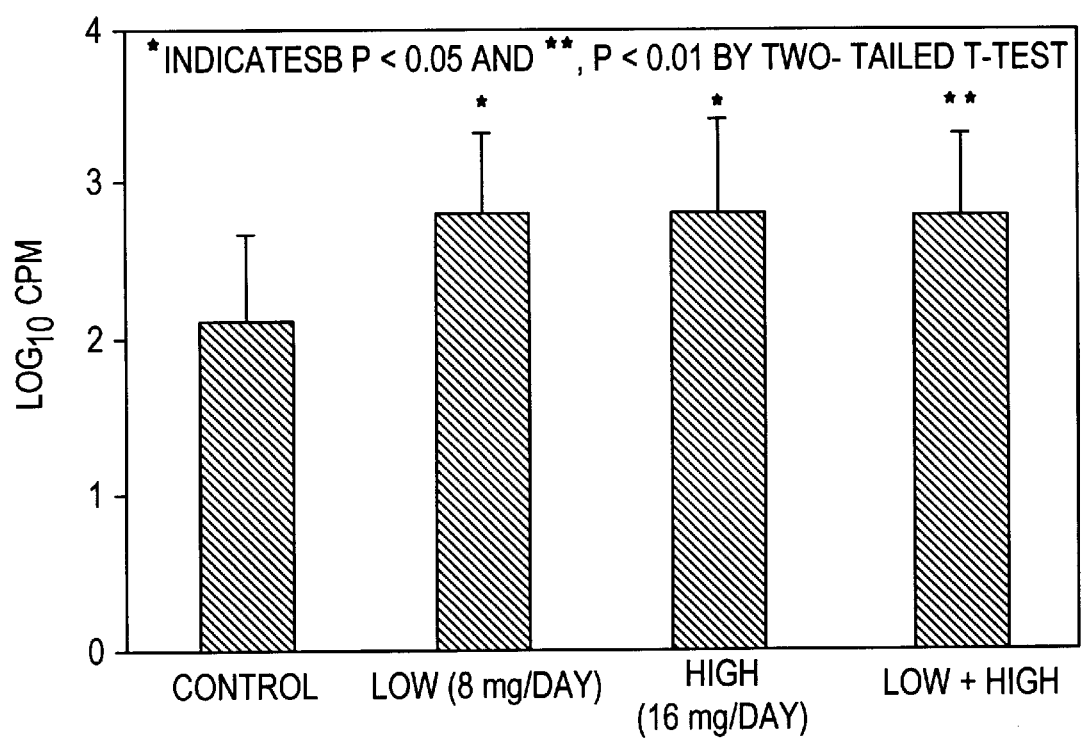

FIG. 7. Phytohemagglutinin (PHA) stimulated lymphocyte proliferation in W/Fu female rats supplemented with C-MED-100 extract (Example 1) for 8 and 16 mg/day for 8 consecutive weeks. Splenocytes were prepared by single cell suspension (Olsson et al., 1995, Carcinogenesis 16(5): 1029–1035) and cultured on a microliter plate at 25,000 cells/well in 200 μl RPMI 1640- 10% fetal calf serum-10 μl PHA at 37° C., 5% $CO_2$ for 5 days, then pulsed for 6 hours with 0.5 μCi [$^3$H]thymidine/ml. Labeled nuclear material was collected on glass fiber filters in a microliter plate cell harvester, dried and counted in scintillation fluid. The resulting cpm [$^3$H]thymidine data was log-transformed to get a near normal distribution. Results are shown by average in column and SD in error bar. n=5 in each group except (low+high)n=10.

DETAILED DESCRIPTION OF THE INVENTION

The following examples are some preferred features but not limitations of this invention.

EXAMPLE 1

Preparation of Uncaria extracts (C-Med-100). One hundred and fifty grams of air-dried bark (collected from Campa Indians by CampaMed, Inc., Arlington, Vt.) or pulverized bark powder (supplied commercially by MW International, Inc., Hillside, N.J.) of Uncaria (Willd), also known commonly as Una de Gata or Cat's Claw, were mixed with 5 liters of tap water and heated in a stainless steel pot to the subboiling point (about 90–100° C.) for 20–24 hours until the hot water extract was concentrated to about 900–1000 milliliters by evaporation. The dark brown extract was then adjusted to exactly 1000 milliliters, filtered through common coffee filters (Melitta Scandinavia AB), and then centrifuged at 3000×g for 15 minutes at 40° C. to produce a particulate-free water extract equal to 150 grams crude bark per 1000 milliliters or 0.15 grams per milliliter. Next 50 milliliter aliquots of the water extract were transferred into cellulose membrane dialysis tubing (pore size 2.4 nm, exclusion limit=<12 000 molecular weight, KEBO Lab) and dialyzed against 1000 milliliters distilled water for 24 hours at 4° C. After dialysis, the high molecular weight fraction (dark brown) retained in the dialysis tubing was discarded and the low molecular fraction (light yellow) that diffused out was concentrated by a water vacuum evaporation at 50° C. to equal a volume of 50 milliliters. It is this preparation of a hot water, dialyzable (low molecular weight) extract from Uncaria bark that has been biologically evaluated in this invention and hereby is referred to as C-Med-100 extract.

The C-Med-100 preparation is a pale yellow to light brown clear solution with a slight bitter taste and no odor. UV spectral scanning shows a peak absorption at $A_{199nm}$. C-Med-100 is stable to heat of subboiling for 24 hours and sterilization by autoclaving (20 minutes at 121° C.) and maintains its biological activity for at least 6 months when frozen in liquid form at −20° C. When dried by frozen vacuum evaporation, light brown particles are produced yielding 7.933±0.249 milligrams per milliliter of the hot water, dialyzed extract. Hence, the yield from crude bark was 7.933 mg per milliliter divided by 150 mg per milliliter or 5.3%.

EXAMPLE 2

Anti-tumor activity of Uncaria extract (C-Med-100). The anti-tumor activity of C-Med-100 extract prepared as in Example 1 was evaluated in vitro using 2 human leukemic cell lines (HL-60 and K-562) and a mouse leukemic cell line (Raji). The anti-proliferative potency of C-Med-100 was assessed by counting the total number of cells by microscopic analysis at 400×magnification. The cancer cell lines were seeded in duplicate 2 milliliter cultures at a cell density of $0.5 \times 10^5$ cells per culture in 15 milliliter Falcon test tubes. The culture medium was RPMI with 10% fetal calf serum and the test tubes were incubated under standard conditions (i.e. 37° C., 5% $CO_2$ and 80% humidity). C-Med-100 extract was added at 198 and 397 μg per milliliter together with the cell seeding, and the incubation was continued for 8 days. The total number of cells in each culture was determined every day by hemocytometer counting in the presence of trypan blue. After 8 days of growth assessment, the cultures receiving 397 μg per milliliter of C-Med-100 extract were spun down, the old culture medium discarded and new culture medium added back containing ±397 μg per milliliter C-Med-100 extract. This was done to ascertain if the cells surviving 397 μg per milliliter C-Med-100 were actually killed (cytotoxic) or only growth inhibited (cytostatic).

The data presented in FIG. 1 clearly shows that C-Med-100 extract has a profound anti-proliferative effect on all three cancer cell lines. Interestingly, K-562 cells, well known to be resistant to induction of apoptosis (D'Amico and McKenna, Radiother. Onocol. 33:3–10, 1994), were also the most resistant to growth inhibition using C-Med-100 extract. This data supports the effects on apoptosis presented in Example 3. Furthermore, the regrowth experiments in FIG. 1 indicate that not all phases of the cell cycle of cancer cells are equally susceptible to C-Med-100 extract. It was shown that even when growth was inhibited >95% over an 8 day period in culture, as was the case with HL-60 and Raji cells, when C-Med-100 extract was removed from the medium at least some cells began to grow after a few more days in culture. This data is consistent with Example 3 and also teaches that some tumor cells must be in a state of growth such that they are resistant to C-Med-100 extract and not capable of undergoing death by apoptosis.

EXAMPLE 3

Induction of apoptosis by Uncaria extracts (C-Med-100). Apoptosis is a natural occurring form of cell death or suicide of particular significance to maintaining competent homeostatic inflammatory and immune responses necessary as a primary defense against many diseases including cancer, viral infections, AIDS, autoimmune and neurodegenerative disorders. Agents that can induce apoptosis are potential anti-inflammatory and anti-tumor drugs because they may have the ability to induce apoptotic death in malignant or inflammatory macrophages or monocytes which are known to be particularly sensitive to induction of apoptosis. Likewise, such agents simultaneously stimulate immune cell function by limiting or reducing the production of TNF-Δ by the inflammatory cells which are a well known natural occurring agent that is cytotoxic to lymphocytes and thus immunosuppressive (Apoptosis reviewed by C. B. Thompson, Science 267:1456–62, 1995). The data in this Example (FIG. 2) demonstrates and discloses that C-Med-100 extract of Uncaria described in Example 1 is an effective inducer of apoptosis in HL-60 leukemic cells, and thus this preparation possesses important anti-tumor, anti-inflammatory and immune stimulating properties.

For the purpose of evaluating apoptosis in vitro, human leukemic HL-60 cells were cultured at a density of $0.5 \times 10^6$ cells per milliliter in 10% calf serum supplemented RPMI medium in a 5% $CO_2$ atmosphere at 37° C. for 48 hours. The cells were harvested by centrifugation and resuspended in a fresh medium at a concentration of $1-2 \times 10^6$ cells per milliliter in 15 milliliter Falcon test tubes for bioassay purposes. Next the cells were exposed to either 100 μM hydrogen peroxide as a positive control or 397 μg per milliliter C-Med-100 extract prepared according to Example 1 or no exposure for 0–72 hours at 37° C. Samples of cells were taken from the cultures at the time periods indicated in FIG. 2 and the % apoptosis in the total cells counted were analyzed and scored by phase contrast morphological criteria.

EXAMPLE 4

Relative cytotoxic dose potency of crude bark versus Uncaria hot water extraction (C-MED100). Commercial preparations of Uncaria are formulated and sold as crude bark phytomedicines given orally usually in capsules at the dose of 1–3 grams per day. The bioavailability of ingested crude bark has never been determined but necessarily would rely on an efficient extraction and absorption of the active components under the acidic conditions of the stomach. On the other hand, C-Med-100 water extract would not have its bioavailability influenced by the particulate fraction of Uncaria. To estimate the relative bioavailabilities of these two preparations of Uncaria, dose response antiproliferative activities were evaluated against leukemic HL-60 cells.

Crude bark material was first extracted with 1 N HCl for 3 hours at a concentration of 0.15 grams per milliliter which was identical to the concentration of crude bark used to produce C-Med-100 extract. Next, this acid extract was neutralized with 5 N NaOH, centrifuged at 3000 ×g to remove particulate material, and the supernatant (soluble fraction) used for comparison with C-Med-100 extract. C-Med-100 extract prepared as in Example 1 was treated in the same exact way as the acidic crude bark preparation so that they could be compared under controlled extraction procedures for biological activity.

The ability of these two Uncaria preparations to inhibit the proliferation of HL-60 cells was determined using exponentially growing HL-60 cells cultured at the density of 50,000/milliliter in RPMI 1640 medium with 10% fetal calf serum, and±mixed with the two different Uncaria preparations in a volume of 50 μl per 950 μl of culture to equal the final concentrations for the data points reported in FIG. 3 (i.e. 0–600 μg of the dry weights of the respective acidic aqueous extracts per milliliter). 200 μl of the±treated cells suspensions were seeded in 96-well microliter plates and cultured in an incubator at 37° C. with 6% $CO_2$ and 80% humidity for 3 days. Aliquots of 25μl [$^3$H]thymidine (9 μCi/milliliter) were added for another 60 minutes before the cells were harvested by vacuum aspiration onto glass fiber filters (Whatman GF/A). While free [$^3$H ]thymidine is washed through the filters, the [$^3$H]thymidine incorporated into deoxyribonucleic acid (DNA) is retained. The radioactivity retained on the filters was quantified by liquid scintillation counting.

EXAMPLE 5

In vivo evaluation of toxic side effects and hematologic parameters of Uncaria extract (C-Med-100). This invention discloses not only a unique composition of, and a preparation for, Uncaria but also that the current phytomedicinal practice is not consistent with achieving efficacious treatments of humans based on the daily doses of crude bark recommended for oral administration. As already pointed out in this invention, to achieve single efficacious doses of Uncaria judged by induction of apoptosis or inhibition of cell proliferation (Examples 2 and 3), at least 262 to 524 grams of crude bark (calculation presented in summary of the invention section) would need to be ingested every day. However, C-Med-100 extract could easily be administered orally at these dose levels in one capsule, tablet or the equivalent. In order to evaluate the toxicological and immunological consequences of dosing C-Med-100 extract prepared as in Example 1 in this concentration range, W/Fu rats initially weighing 150–200 grams were administered daily doses of C-Med-100 extract by oral gavage over an 8 consecutive week period. The rats were kept in ambient temperature of 21° C. to 23° C. Lights were kept on from 6 am to 6 pm and the rats were given free access to fresh tap water and standard pellet food and were genetically assigned as a health check. The protocol contained 30 female rats randomly assigned into 3 groups each composed of 10 animals: Group 1=controls, 1 milliliter sterile water by oral gavage; Group 2=8 mg dried weight of C-Med-100 extract per milliliter by oral gavage; Group 3=16 mg dried weight of C-Med-100 extract per 2 milliliters by oral gavage. Acute toxicity was monitored every day by the presence or absence of symptoms. Body weight was recorded once per week, and hematological parameters were measured every second week. About 0.3 ml blood sample was taken from the optical venous plexus of the rat into 2 ml polypropylene microcentrifuge tube containing 25 $\mu$l 2500 I.E. heparin per milliliter (200 I.E./ml in final concentration) and then immediately analyzed by an automated hematology analyzer (Sysmex, K-1000).

The relevant in vivo data is presented in FIGS. 4 and 5. No acute symptoms were observed so far in the rats after 6 weeks of daily C-Med-100 oral administration at the 8 or 16 mg daily doses. All the rats gained weight over the experimental period and no statistical difference was found at any of the time points tested among the 3 groups (FIG. 4). These data teach that the relatively high doses of C-Med-100 extract, which to our knowledge have never previously been administered in vivo for Uncaria preparations, are safe and free from causing any gross obvious acute or chronic toxic response.

In addition, both the 8 and 16 mg doses of C-Med-100 extract showed a statistically significant increase in hemoglobin ($p<0.0001$ for both groups by one tailed t-test) and white blood cell counts ($p<0.05$ and $p<0.077$ by one tailed t-test) (FIG. 5). Increased hemoglobin could be stimulatory to respiration and energy production while elevations in the constitutive WBC could have immune enhancing effects both of which were induced by the C-Med-100 intervention. Hence, the data in FIGS. 4 and 5, taken together with that reported in FIGS. 1 and 2, disclose that doses of C-Med-100 inducing favorable in vitro biological responses are also both safe and effective in vivo.

EXAMPLE 6

DNA repair enhancement by C-MED-100 supplementation in rat module. This example teaches that in vivo supplementation of 8 or 16 mg/day C-MED-100 extract for 8 consecutive weeks in the rat resulted in an enhanced ability to carry out DNA repair and thereby to remove DNA damage that in turn inhibits cell replication and immune function. This data confirms that C-MED-100 extract supplementation has the ability to stimulate the removal of DNA lesions that can cause human disease such as cancer as well as stimulate immune cell responsiveness.

EXAMPLE 7

PHA stimulated lymphocyte proliferation in W/Fu female rats supplemented with C-MED100. This example discloses the immune stimulating properties of C-MED-100 extract supplemented in vivo with 8 or 16 mg/day. Splenocytes from the C-MED-100 treated rats had an enhanced ability to respond to the growth stimulation induced by the mitogen, PHA.

Various modifications of the methods of preparation, use and composition of the water soluble extract of Uncaria tomentosa shown and described herein, will be readily apparent to those skilled in the art from the foregoing descriptions. Such modifications are also intended to fall within the scope of the appended claims.

What is claimed is:

1. A method for preparing a water soluble extract of an Uncaria species comprising:
   (a) heating a mixture of water and a substance selected from the group consisting of dried roots, bark and bark powder of said Uncaria species at a temperature of approximately 90–100° C. for such a time and at such a ratio of said substance to said water to yield a first brown extract of said mixture due to evaporation of said water;
   (b) filtering said first brown extract from said mixture;
   (c) centrifuging said filtered brown extract;
   (d) dialyzing said centrifuged brown extract against distilled water in a dialysis tubing having an exclusion limit of up to approximately 12,000 molecular weight at approximately 4–15° C. for 20–48 hours to separate a water soluble extract of said Uncaria species; and
   (e) recovering said separated water soluble extract of an Uncaria species.

2. The method of claim 1 wherein said substance selected from the group consisting of bark and bark powder of said Uncaria species is mixed with water at a ratio of 150 grams of bark or bark powder to 5 liters of water.

3. The method of claim 1 wherein said Uncaria species is selected from the group consisting of *tomentosa, guianensis, pteropoda, homomalla, perrottetii* and *rhynchopylla*.

4. The method of claim 1 wherein the step of centrifuging takes place at 1000–3000 ×g for 15–60 minutes.

5. The method of claim 1 wherein the step of dialyzing said centrifuged brown extract against said distilled water takes place at a volume of 50–100 milliliters of said particulate free water extract per 500–1500 milliliters of said distilled water.

6. A water soluble extract of an Uncaria species obtained by the method of claim 1 wherein said extract:
   (a) exhibits UV maxima at approximately 199 nm;
   (b) is stable to temperatures less than 100° C. for 24 hours and sterilization by autoclaving for up to at least 20 minutes at approximately 121° C.;
   (c) maintains biological activity for at least 6 months when frozen in liquid form at approximately −20° C.; and
   (d) consists essentially of molecules having a molecular weight of up to approximately 12,000.

7. A water soluble extract of an Uncaria species obtained by the method of claim 1.

8. A pharmaceutical composition comprising:
   (a) the water soluble extract of an Uncaria species of claim 7; and
   (b) a nontoxic inert carrier or diluent.

9. The pharmaceutical composition of claim 8 wherein said carrier or diluent is selected from the group consisting of wheat starch and sodium carboxy methyl cellulose.

10. A method for enhancing the immune competency of a mammal by inhibiting TNF-α production or inducing apoptosis of white blood cells comprising administering to said mammal the pharmaceutical composition of claim 8 in an amount effective to inhibit TNF-α production or to induce apoptosis of white blood cells.

11. The method of claim 10 wherein said mammal is a human.

12. The method of claim 10 wherein the step of administering said pharmaceutical composition is orally and wherein said pharmaceutical composition is in a form selected from the group consisting of capsules, tablets, syrups, and liquids.

13. A method for inhibiting the inflammatory response of a mammal by inhibiting TNF-α production or inducing apoptosis of white blood cells comprising administering to said mammal the pharmaceutical composition of claim 8 in an amount effective to inhibit TNF-α production or to induce apoptosis of white blood cells.

14. The method of claim 13 wherein said mammal is a human.

15. The method of claim 13 wherein the step of administrating said pharmaceutical composition is orally and wherein said pharmaceutical composition is in a form selected from the group consisting of capsules, tablets, syrups, and liquids.

16. A method for decreasing the proliferation of leukemic cells in a mammal comprising administering to said mammal an effective amount of the pharmaceutical composition of claim 8.

17. The method of claim 16 wherein said mammal is a human.

18. The method of claim 16 wherein the step of administering said pharmaceutical composition is orally and wherein said pharmaceutical composition is in a form selected from the group consisting of capsules, tablets, syrups, and liquids.

* * * * *